(12) United States Patent
Saxer et al.

(10) Patent No.: US 8,797,530 B2
(45) Date of Patent: Aug. 5, 2014

(54) LINEARIZED VARIABLE-DISPERSION SPECTROMETERS AND RELATED ASSEMBLIES

(75) Inventors: Christopher Saxer, Chapel Hill, NC (US); Robert H. Hart, Cary, NC (US); Eric L. Buckland, Hickory, NC (US); Pete Huening, Clayton, NC (US); Bradley A. Bower, Hillsborough, NC (US)

(73) Assignee: Bioptigen, Inc., Durham, NC (US)

( * ) Notice: Subject to any disclaimer, the term of this patent is extended or adjusted under 35 U.S.C. 154(b) by 0 days.

(21) Appl. No.: 13/428,247

(22) Filed: Mar. 23, 2012

(65) Prior Publication Data

US 2012/0242988 A1 Sep. 27, 2012

Related U.S. Application Data

(60) Provisional application No. 61/466,611, filed on Mar. 23, 2011.

(51) Int. Cl.
*G01J 3/28* (2006.01)

(52) U.S. Cl.
USPC ........................................ 356/328

(58) Field of Classification Search
USPC ........................................ 356/326
See application file for complete search history.

(56) References Cited

U.S. PATENT DOCUMENTS

| | | | |
|---|---|---|---|
| 5,270,842 A * | 12/1993 | Clay et al. | 359/12 |
| 6,661,513 B1 | 12/2003 | Granger | |
| 7,903,257 B2 | 3/2011 | de Boer et al. | |
| 8,348,427 B2 | 1/2013 | Buckland et al. | |
| 8,625,104 B2 | 1/2014 | Izatt et al. | |
| 2002/0039231 A1 | 4/2002 | Sela | |
| 2006/0164639 A1 | 7/2006 | Horn et al. | |
| 2007/0030484 A1* | 2/2007 | Sobczynski | 356/328 |
| 2008/0088928 A1 | 4/2008 | Tedesco | |
| 2009/0040521 A1* | 2/2009 | Hu et al. | 356/328 |

OTHER PUBLICATIONS

Invitation to Pay Additional Fees, PCT/US2012/030251, Jun. 19, 2012.
Hu et al., "Fourier domain optical coherence tomography with a linear-in-wavenumber spectrometer," Optics Letters, vol. 32, No. 24, Dec. 15, 2007, pp. 3525-3527.
Traub, Wesley A., "Constant-dispersion grism spectrometer for channeled spectra," J. Opt. Soc. Am. A, vol. 7, No. 9, Sep. 1990, pp. 1779-1791.
Geilkonov et al., "Linear-Wavenumber Spectrometer for High-Speed Spectral-Domain Optical Coherence Tomography," May 2008.

(Continued)

*Primary Examiner* — Tarifur Chowdhury
*Assistant Examiner* — Abdullahi Nur
(74) *Attorney, Agent, or Firm* — Myers Bigel Sibley & Sajovec

(57) ABSTRACT

Wavenumber linear spectrometers are provided including an input configured to receive electromagnetic radiation from an external source; collimating optics configured to collimate the received electromagnetic radiation; a dispersive assembly including first and second diffractive gratings, wherein the first diffraction grating is configured in a first dispersive stage to receive the collimated electromagnetic radiation and wherein the dispersive assembly includes at least two dispersive stages configured to disperse the collimated input; and an imaging lens assembly configured to image the electromagnetic radiation dispersed by the at least two dispersive stages onto a linear detection array such that the variation in frequency spacing along the linear detection array is no greater than about 10%.

18 Claims, 15 Drawing Sheets

(56) References Cited

OTHER PUBLICATIONS

Notification of Transmittal of the International Search Report and the Written Opinion of the International Searching Authority, PCT/US2012/030261, Aug. 1, 2012.

Gelikonov et al., "Linear-Wavenumber Spectrometer for High-Speed Spectral-Domain Optical Coherence Tomography," Optics and Spectroscopy, 2009, vol. 105, No. 3, pp. 459-465, 2009.

Notification Concerning Transmittal of International Preliminary Report on Patentability, PCT/US2012/030251, Sep. 24, 2013, 11 pages.

* cited by examiner

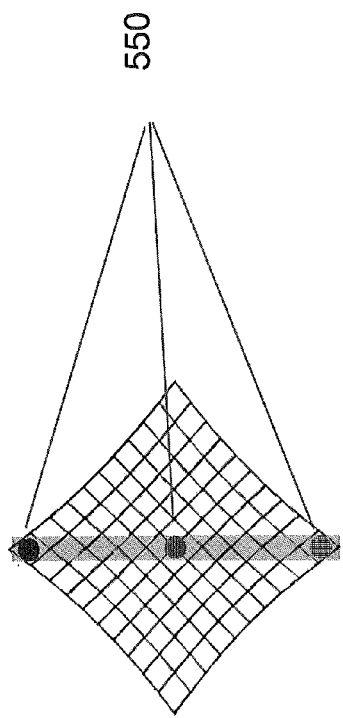
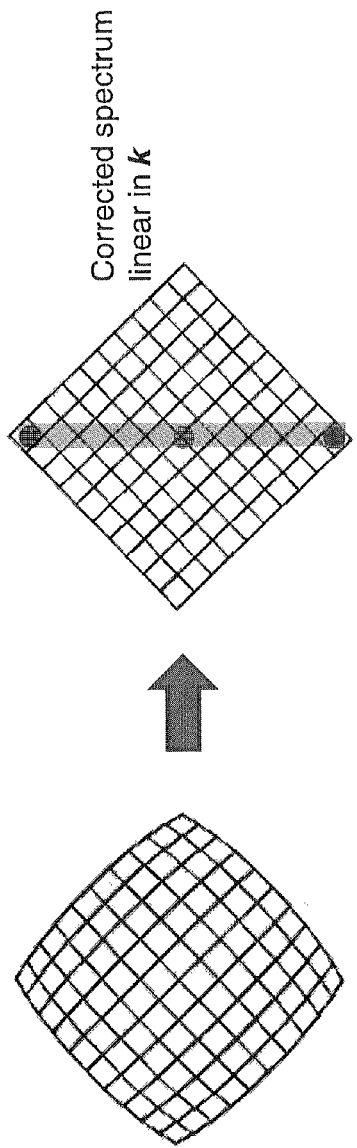
Figure 5A
Figure 5B

| Spectrometer depth range (mm) | Wavenumber span (1/cm) | λmin (nm) | λmax (nm) | λo (nm) | Dispersion at image plane (mm cm) |
|---|---|---|---|---|---|
| 2 | 5030 | 610 | 880 | 720 | 0.0031 |
| 4 | 2590 | 750 | 930 | 830.4 | 0.0155 |
| 8 | 1295 | 830 | 930 | 877.2 | 0.0311 |
| 16 | 648 | 877 | 930 | 902.7 | 0.0622 |
| 40 | 259 | 908 | 930 | 918.9 | 0.1554 |

| Spectrometer depth range (mm) | Configuration | Grating (lpmm) | Prism apex angle (deg) | Angle of incidence |
|---|---|---|---|---|
| 2 | Grating - prism - grating | 1504 / 956 | 31.5 | 34.6 (G1) / 21.4 (Prism) / -19.0 (G2) |
| 4 | Grism | 770 | 32.6 | 50.5 |
| 8 | Grism | 1504 | 60 | 44.1 |
| 16 | Grating - grism | 1504 (G1) / 1504 (G2) | NA / 60.0 | 43.4 (G1) / 46.6 (G2) |
| 40 | Dual grism | 2189 (G1) / 2189 (G2) | 85.5 / 85.5 | 67.2 (G1) / 60.0 (G2) |

Figure 13

LINEARIZED VARIABLE-DISPERSION SPECTROMETERS AND RELATED ASSEMBLIES

CLAIM OF PRIORITY

The present application claims priority from U.S. Provisional Application No. 61/466,611, filed Mar. 23, 2011, the disclosures of which are hereby incorporated herein by reference as if set forth in their entirety.

STATEMENT OF GOVERNMENT SUPPORT

This invention was made with government support under grant number 2R44EY018021 awarded by National Institute of Health, National Eye Institute. The United States Government has certain rights in this invention.

FIELD

The present inventive concept generally relates to imaging and, more particularly, to Fourier domain optical coherence tomography (FDOCT) and related systems and methods.

BACKGROUND

Dispersive optical elements disperse light by deviating the path of light passing through them by an amount that varies with wavelength. Prisms and gratings are two types of dispersive optical elements. In particular, prisms disperse light because their geometry causes light of different wavelengths passing through them to be separated and deviated by different amounts. In diffraction gratings, light passing through the grating is diffracted into a series of orders caused by the interference of wavefronts emitted from each slit in the grating.

Dispersive optical elements are used in spectrometers. Spectrometers are used in fields including medicine, material sciences, chemistry, environmental sciences, and so on. Spectrometers use diffractive and refractive dispersive optical elements including gratings and/or prisms to facilitate analyzing the spectral composition of sampled light.

As illustrated in FIG. 1, a conventional spectrometer 110 includes a light input entrance element 112 (Detector arm fiber) for receiving light from an external source. More generally the light entrance element 112 may be referred to as an electromagnetic radiation entrance. The light is passed through a first set of collimating optics 114 (collimating lens) to a diffraction grating 116. The diffraction grating 116 separates the light into various spectra. The separated light passes through a second set of focusing optics 118 to a detection element 120 (detector).

Fourier-domain optical coherence tomography (FDOCT) uses a Fourier transform of spectrum to calculate distribution of scatterers in a sample. Digital Fourier transform algorithms typically rely on data that is evenly spaced in frequency. However, gratings (for example, diffraction grating 116) disperse spectrum proportional to wavelength, not frequency. Thus, as illustrated in FIG. 2A, even spaced frequencies do not have even spacing on the detector 220 in a conventional spectrometer 210. Thus, as illustrated in the graph of FIG. 2B, conventional spectrometers 210 may experience about a 50% change in dispersion across a full spectrum.

U.S Patent Application Publication No. 2009/0040521 entitled EVEN FREQUENCY SPACING SPECTROMETER AND OPTICAL COHERENCE TOMOGRAPHY DEVICE to Hu et al. addresses this relatively high change in dispersion by a prism air-spaced with respect to a grating. This is also discussed in FOURIER DOMAIN OPTICAL COHERENCE TOMOGRAPHY WITH A LINEAR-IN-WAVENUMBER SPECTROMETER by Hu et al. Hu discusses using first and second dispersive elements, for example, a grating and a prism, separated by an air gap to approximately linearize the dispersion angle as a function of wavenumber.

However, improved systems for reducing the overall change in dispersion may be desired.

SUMMARY

Some embodiments of the present inventive concept provide wavenumber linear spectrometers including an input configured to receive electromagnetic radiation from an external source; collimating optics configured to collimate the received electromagnetic radiation; a dispersive assembly including first and second diffractive gratings, wherein the first diffraction grating is configured in a first dispersive stage to receive the collimated electromagnetic radiation and wherein the dispersive assembly includes at least two dispersive stages configured to disperse the collimated input; and an imaging lens assembly configured to image the electromagnetic radiation dispersed by the at least two dispersive stages onto a linear detection array such that the variation in frequency spacing along the linear detection array is no greater than about 10%.

In further embodiments, the dispersive assembly may include a prism. The variation in frequency spacing along the detection array may be no greater than 5.0%.

In still further embodiments, the imaging lens assembly may be configured to image with pincushion distortion. The imaging lens assembly may further include pincushion distortion correction; the presence of the pincushion distortion correction may further reduce the variation in frequency spacing along the detection array to no greater than about 1.0%. The pincushion distortion correction may include a wavefront modifier element positioned after a lens set that images with pincushion distortion and before a detector array. In certain embodiments, the wavefront modifier element may be an asphere.

In some embodiments, the dispersive assembly may be configured to be interchangeable.

In further embodiments, a wavenumber span ranges from about 250 cm$^{-1}$ to about 5100 cm$^{-1}$.

Still further embodiments provide wavenumber linear spectrometers including an input configured to receive electromagnetic radiation from an external source; collimating optics configured to collimate the received electromagnetic radiation; a dispersive assembly including first and second dispersive elements, wherein the first dispersive element is a diffraction grating configured to receive the collimated electromagnetic radiation and wherein the second dispersive element is a refractive prism; and an imaging lens assembly including pincushion distortion correction, wherein the imaging lens assembly is configured to image the collimated electromagnetic radiation dispersed by the dispersive assembly onto a linear detection array, such that the variation in frequency spacing along the linear detection array is no greater than about 5.0%.

In some embodiments, the distortion correction is an asphere positioned after a lens set in the imaging lens system, the presence of the distortion correction further reducing the variation in frequency spacing along the detection array to no greater than about 1.0%.

In further embodiments, the dispersive assembly may be configured to be interchangeable.

In still further embodiments, a wavenumber span may range from about 1000 cm$^{-1}$ to about 3000 cm$^{-1}$.

Some embodiments of the present inventive concept provide spectrometer assemblies including a dispersive assembly including first and second dispersive stages, the first dispersive stage configured to receive a collimated input of electromagnetic radiation; and a lens assembly. The first and second dispersive stages and the lens assembly combine to image the collimated input of electromagnetic radiation dispersed onto a linear detection array, such that the variation in frequency spacing along the detection array is less than about 10%. The dispersive assembly is configured to be interchangeable.

Further embodiments of the present inventive concept provide Fourier domain optical coherence tomography detection systems including a wavenumber linear spectrometer, the wavenumber linear spectrometer including two diffractive gratings.

Still further embodiments of the present inventive concept provide Fourier domain optical coherence tomography detection systems including wavenumber linear spectrometer. The wavenumber linear spectrometer including a diffraction grating; a prism; and a lens assembly, the lens assembly comprising pincushion distortion correction.

BRIEF DESCRIPTION OF THE DRAWINGS

The accompanying drawings, which are included to provide a further understanding of the inventive concept and are incorporated in and constitute a part of this application, illustrate certain embodiment(s) of the inventive concept. In the drawings:

FIGS. 5A and 5B are diagrams illustrating using barrel distortion to compensate for pincushion distortion in accordance with some embodiments of the present inventive concept.

FIG. 13 is a table illustrating various specifications for the various dispersive assembly embodiments in accordance with various embodiments of the present inventive concept.

DETAILED DESCRIPTION

Figure 1:
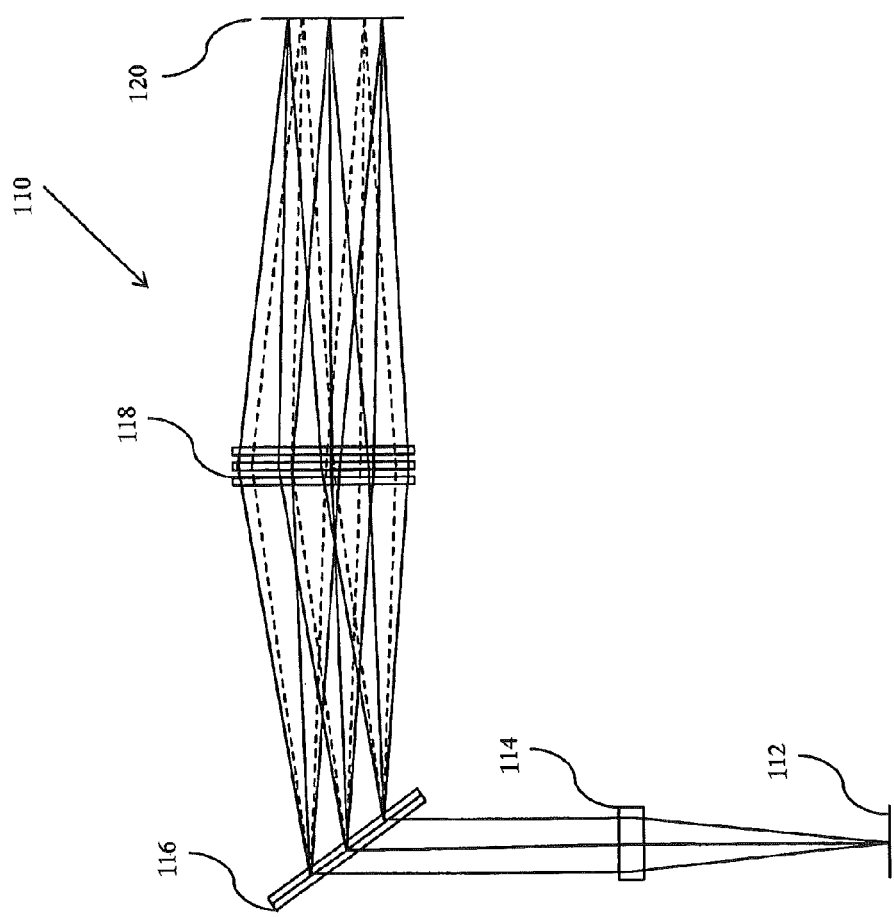
FIG. 1 is a diagram illustrating a conventional spectrometer.
Figure 2:
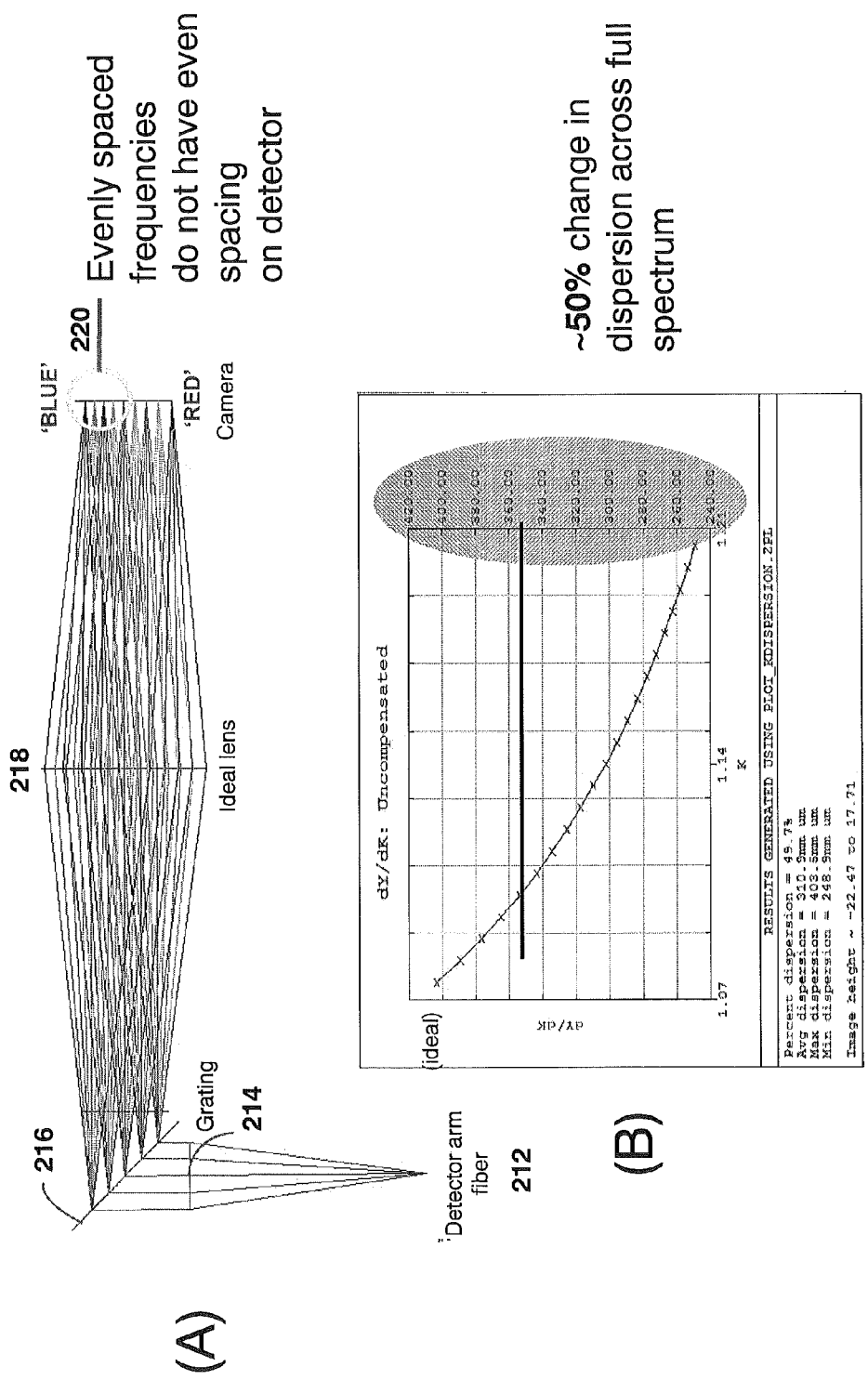
FIG. 2A is a diagram illustrating a conventional spectrometer having uneven spacing at the detector of the spectrometer.
FIG. 2B is a graph illustrating a change in dispersion for the spectrometer illustrated in FIG. 2A.
Figure 3:
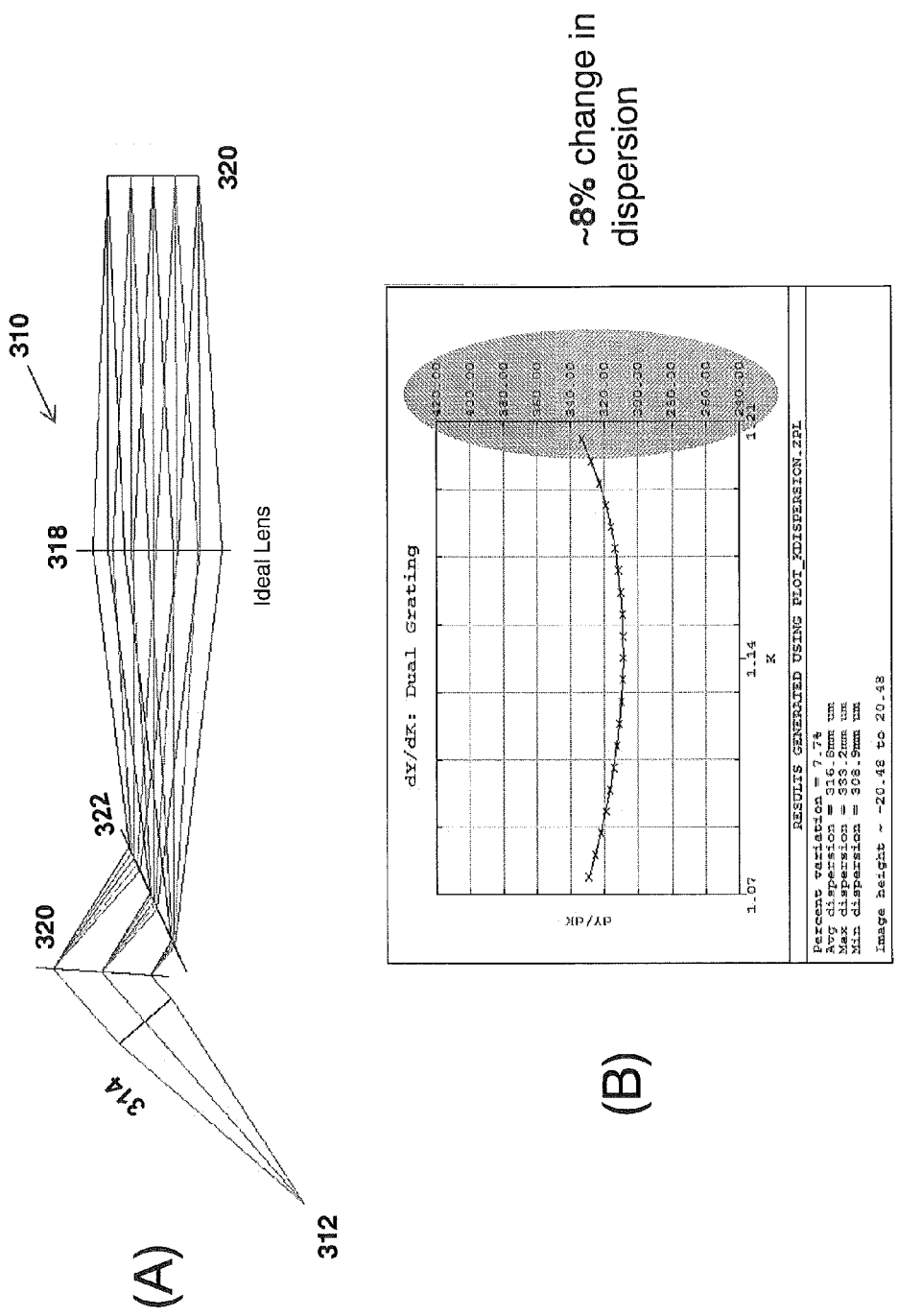
FIG. 3A is a diagram illustrating a spectrometer including a dual grating dispersive assembly in accordance with some embodiments of the present inventive concept.
FIG. 3B is a graph illustrating a change in dispersion for the spectrometer illustrated in FIG. 3A.
Figure 4:
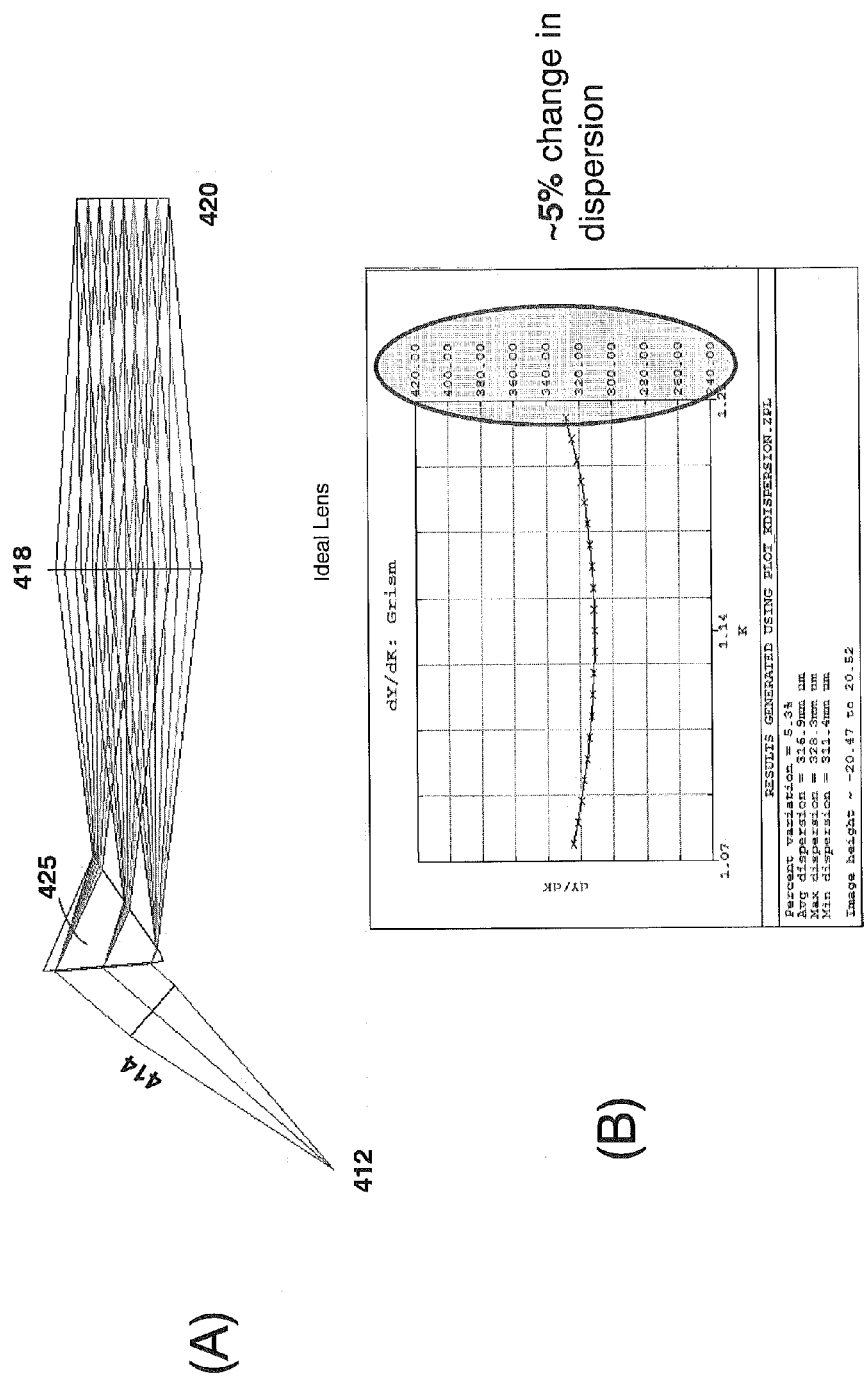
FIG. 4A is a diagram illustrating a spectrometer including a grism dispersive assembly in accordance with some embodiments of the present inventive concept.
FIG. 4B is a graph illustrating a change in dispersion for the spectrometer illustrated in FIG. 4A.
Figure 6:
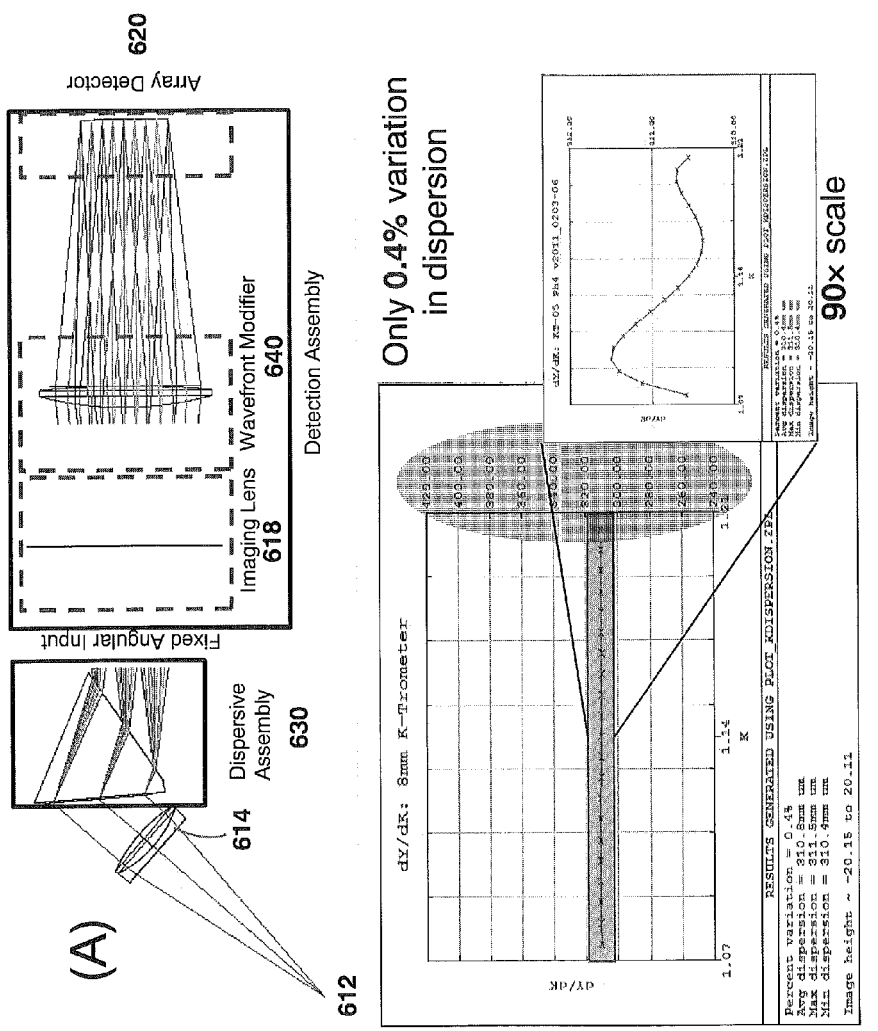
FIG. 6A is a block diagram illustrating a spectrometer including a distortion element in addition to a dispersive assembly in accordance with some embodiments of the present inventive concept.
FIG. 6B is a diagram illustrating a dispersion variation of the spectrometer of FIG. 6A.
Figure 7:
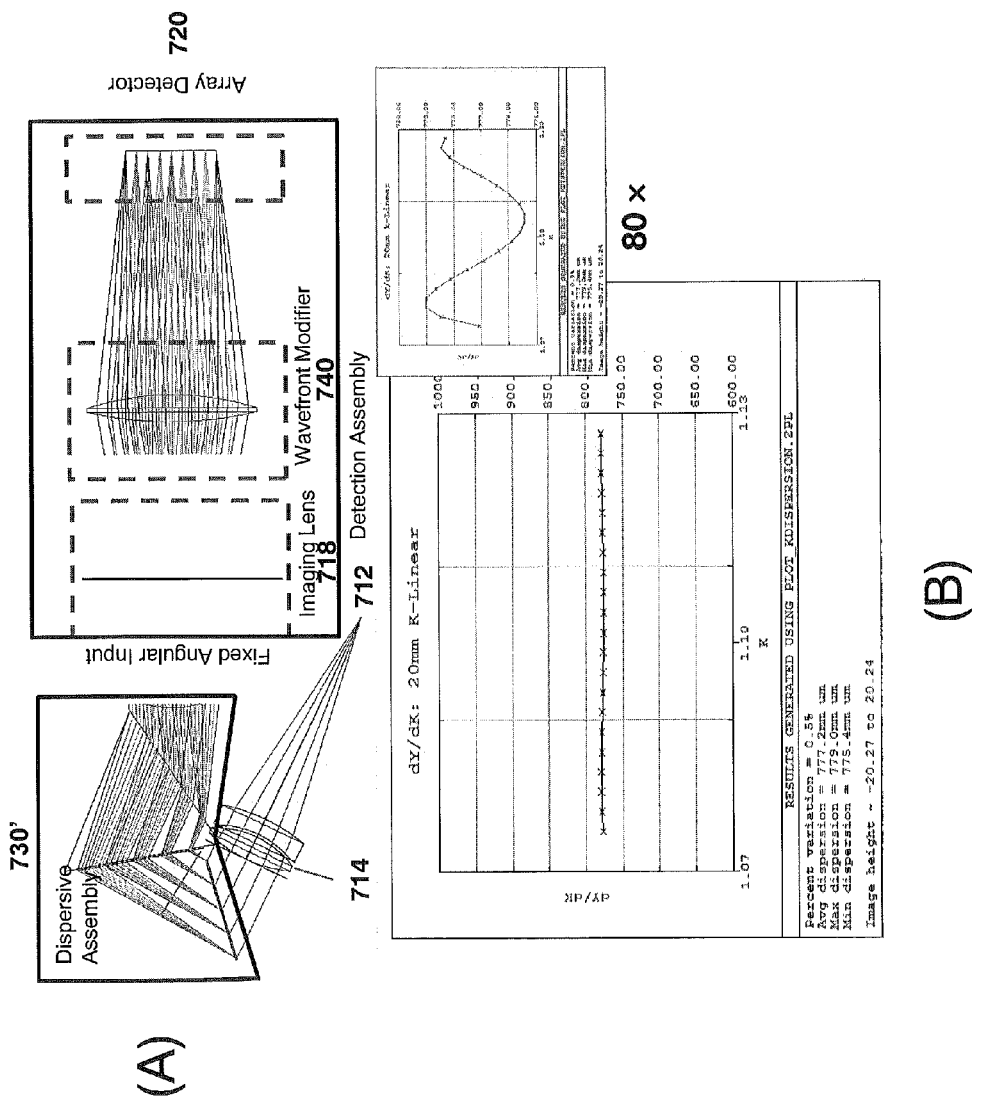
FIG. 7A is a block diagram illustrating a spectrometer including a distortion element in addition to a dispersive assembly in accordance with some embodiments of the present inventive concept.
FIG. 7B is a diagram illustrating a dispersion variation of the spectrometer of FIG. 7A.
Figure 8:
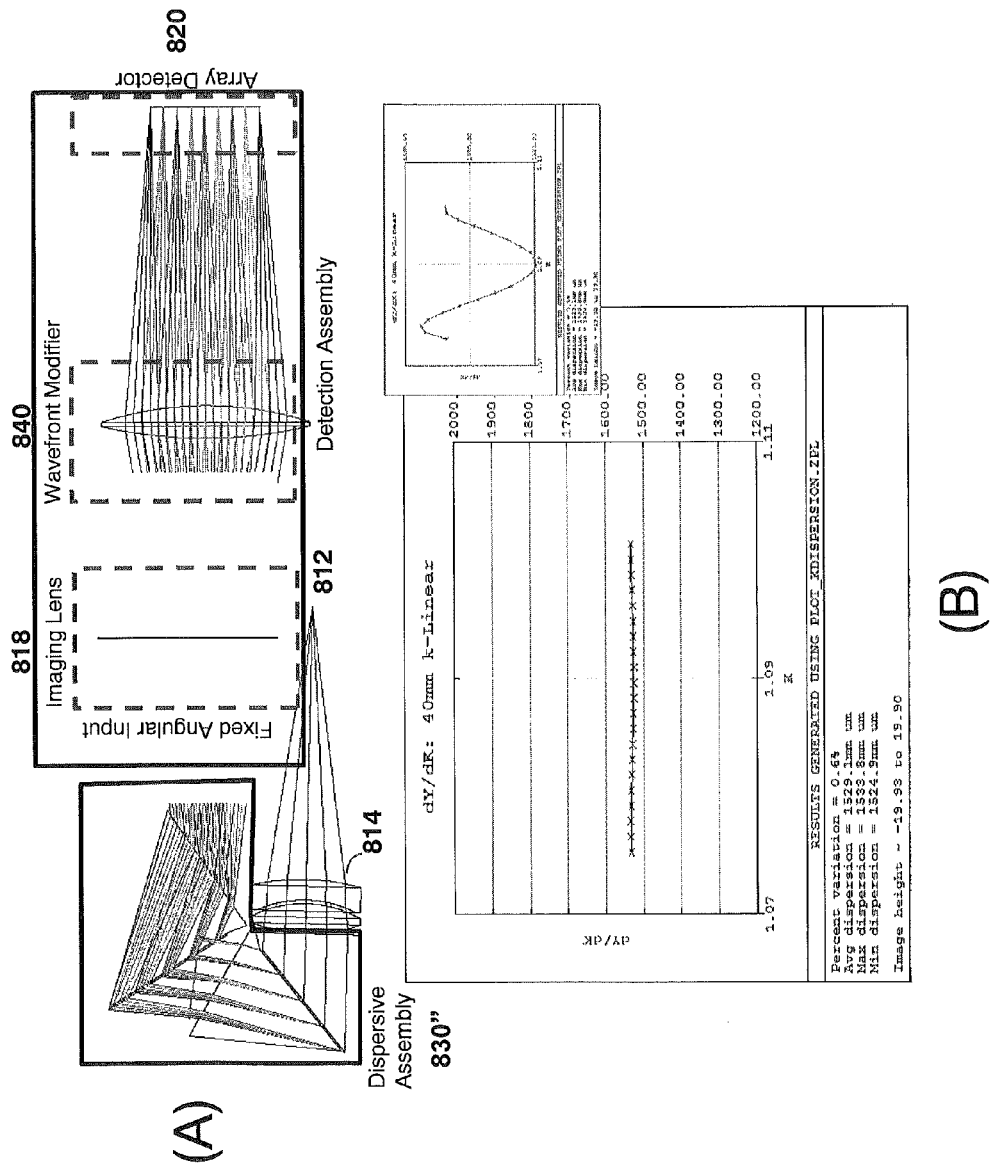
FIG. 8A is a block diagram illustrating a spectrometer including a distortion element in addition to a dispersive assembly in accordance with some embodiments of the present inventive concept.
FIG. 8B is a diagram illustrating a dispersion variation of the spectrometer of FIG. 8A.
Figure 9:
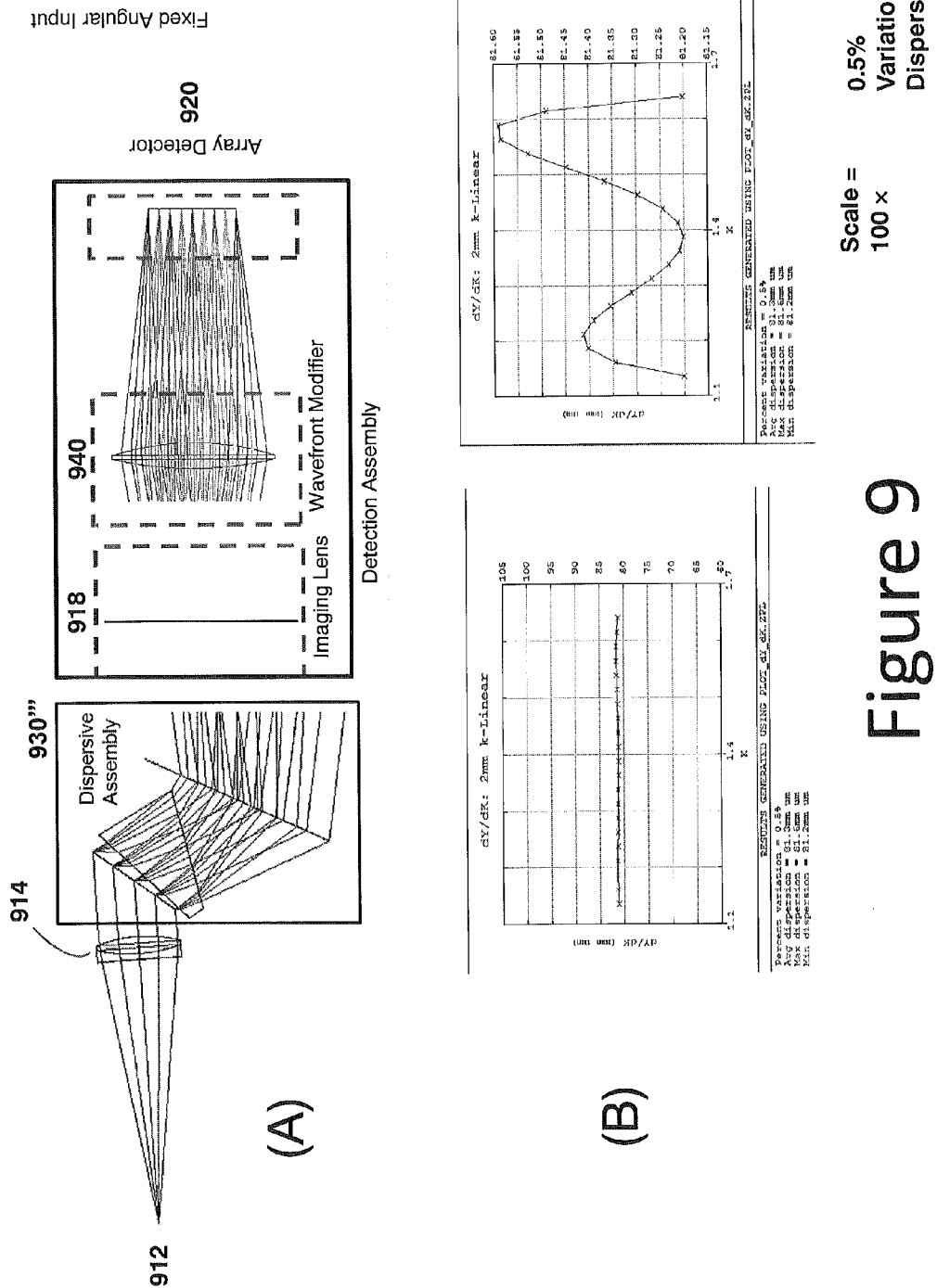
FIG. 9A is a block diagram illustrating a spectrometer including a distortion element in addition to a dispersive assembly in accordance with some embodiments of the present inventive concept.
FIG. 9B is a diagram illustrating a dispersion variation of the spectrometer of FIG. 9A.

The inventive concept will now be described more fully hereinafter with reference to the accompanying drawings, in which embodiments of the inventive concept are shown. This inventive concept may, however, be embodied in many different forms and should not be construed as limited to the embodiments set forth herein; rather, these embodiments are provided so that this disclosure will be thorough and complete, and will fully convey the scope of the inventive concept to those skilled in the art.

It will be understood that, when an element is referred to as being "connected" to another element, it can be directly connected to the other element or intervening elements may be present. In contrast, when an element is referred to as being "directly connected" to another element, there are no intervening elements present. Like numbers refer to like elements throughout.

Spatially relative terms, such as "above", "below", "upper", "lower" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly. Well-known functions or constructions may not be described in detail for brevity and/or clarity.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present inventive concept. As used herein, the term "and/or" includes any and all combinations of one or more of the associated listed items.

Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of this specification and the relevant art and will not be interpreted in an idealized or overly formal sense expressly so defined herein.

Embodiments of the inventive concept are described herein with reference to schematic illustrations of idealized embodiments of the inventive concept. As such, variations from the shapes and relative sizes of the illustrations as a result, for example, of manufacturing techniques and/or tolerances, are to be expected. Thus, embodiments of the inventive concept should not be construed as limited to the particular shapes and relative sizes of regions illustrated herein but are to include deviations in shapes and/or relative sizes that result, for example, from different operational constraints and/or from manufacturing constraints. Thus, the elements illustrated in the figures are schematic in nature and their shapes are not intended to illustrate the actual shape of a region of a device and are not intended to limit the scope of the inventive concept.

As discussed in the background, U.S Patent Application Publication No. 2009/0040521 entitled EVEN FREQUENCY SPACING SPECTROMETER AND OPTICAL COHERENCE TOMOGRAPHY DEVICE to Hu et al. addresses this relatively high change in dispersion by a prism air-spaced with respect to a grating. This is also discussed in FOURIER DOMAIN OPTICAL COHERENCE TOMOGRAPHY WITH A LINEAR-IN-WAVENUMBER SPECTROMETER by Hu et al. Hu discusses using first and second dispersive elements, for example, a grating and a prism, separated by an air gap to approximately linearize the dispersion angle as a function of wavenumber, such that uniform spatial sampling at the detector array equates to sampling at constant frequency, or wavenumber, intervals. However, the use of a grating-air space-prism configuration typically requires control of extra degrees of freedom, and adds to the number of glass-air interfaces, potentially reducing the ease of manufacture and increasing costs.

As originally discussed in CONSTANT-DISPERSION GRISM SPECTROMETER FOR CHANNELED SPECTRA by Traub, a prism-grating (GRISM) structure in intimate contact may be adequate to the task of creating, in the language of Traub, a constant dispersion (k-linear) spectrograph. Traub, however, does not provide a prescription for practical design of a GRISM spectrometer that meets the requirements of FDOCT imaging, including the relationship between required dispersion and degree of linearization required.

Furthermore, Traub's prescription relies on material dispersion of the prism as the primary mechanism of balancing dispersion of the grating. It is however more generally known by Snell's Law that the refraction from the exit face of a prism is a nonlinear function of the angle of incidence to the exit face of the prism and, therefore, that a spectrum with a first angular dispersion impinging onto a face of a prism will transit the prism face with a second angular dispersion, not linearly related to the first. This effect dominates material dispersion for low dispersion glasses. As discussed in, for example, U.S. Pat. No. 6,661,513 to Granger, refractive-diffractive spectrometers use this effect to position a prism after a dispersive grating, but in intimate contact, to achieve a wavelength-linearized dispersion function.

As discussed in U.S. Patent Application Publication No. 2008/0088928 to Tedesco entitled OPTICAL CONFIGURATIONS FOR ACHIEVING UNIFORM CHANNEL SPACING IN WDM TELECOMMUNICATIONS APPLICATIONS, this configuration is sufficiently flexible to achieve a wavenumber-linearized dispersion function and, as such, a function that is more appropriate to systems that rely on frequency-channelized systems than is a wavelength-linearized dispersion function. Hu, as noted, extends this concept to using refraction at two separate faces of a prism, providing an additional degree of freedom for tuning the output dispersion function, but the concept is the same.

Accordingly, some embodiments of the present inventive concept use sequential dispersive functions to both add to total dispersion and to tailor the angular dispersion function. For example, in some embodiments a wavenumber-linearized output function may be achieved using two gratings such that the variation in frequency spacing as imaged along the linear detection array will be no greater than about 10%. In some embodiments, a wavenumber-linearized output may be achieved by following a high dispersion grating with a low dispersion grating, with the relative powers and the angles tuned to the desired function as will be discussed further herein with respect to FIGS. 3 through 15.

One prescription for a two-grating approach to a wavenumber-linearized spectrometer for a bandwidth of from about 830 nm to about 930 nm wavelength is given: the prescription presumes a collimated input of broadband illumination originating in a single-mode optical fiber directed to the input face of a first diffraction grating having a spatial frequency of about 1417 lines per mm. The first-order diffracted beam of the center wavenumber makes an angle alpha_1 relative to the input beam, and is directed at a second diffraction grating angled such that the output angle alpha_2 relative to the original input beam is reduced. In effect, the sign of the diffracted order is inverted after the second grating. The effect is that the total first order dispersive power is approximately the sum of the dispersive powers from the two gratings, but the sign of the derivative of the dispersion with respect to wavelength is flipped, allowing the second grating to compensate for the variation in dispersion induced by the first grating. Appropriate selection of the two gratings enables the system to be designed for targeted total dispersion and for approximately constant dispersion with respect to, for example, wavenumber.

Referring now to FIG. 3A, embodiments of the present inventive concept including a dual grating dispersion assembly will be discussed. As illustrated in FIG. 3A, the spectrometer 310 includes a light entrance element 312 (Detector arm fiber) for receiving light from an external source. More generally the light entrance element 312 may be referred to as an electromagnetic radiation entrance. The light is passed through a first set of collimating optics 214 (collimating lens) to a dispersive assembly 330 including first and second gratings 320 and 322 in accordance with some embodiments discussed herein. The first and second gratings 320 and 322 separate the light into various spectra. The separated light passes through a second set of focusing optics 318 to a detection element 320 (detector). As used herein, the "focusing optics" 318 will be assumed to be an ideal lens set. As is understood by those having skill in the art, many different lens sets can be used for the focusing optics 318 of the Spectrometer 310 without departing from the scope of the present inventive concept.

Details of some exemplary embodiments illustrated in FIG. 3A will be discussed. The spectral bandwidth is 100 nm, 1295 cm$^{-1}$ (inverse centimeters) centered at 880 nm. The first grating 320 with 1417 lines/mm at a 45 degree angle of incidence is followed by the second grating 322 of 484 lines/mm at a 29 degree angle of incidence. The angle between grating 1 and grating 2 is 61.4 degrees. The first grating 320 is at angle of 45 degrees with respect to the input beam. The output from the second grating is imaged onto a linear array. As illustrated in FIG. 3B, the spatial increment with respect to wavenumber increment is constant to within 8.0%, exhibiting a characteristic quadratic distortion. In other words, using a dual-grating dispersive assembly 330 as illustrated in FIG. 3A may lower the variation in dispersion to about 8.0%.

Referring now to FIG. 4A, embodiments of the present inventive concept using a GRISM as the dispersive assembly will be discussed, such that the variation in frequency spacing as imaged along the linear detection array will be no greater than about 5%. It will be understood that like reference numerals refer to like elements throughout. Therefore details with respect to these elements may not be repeated herein in the interest of brevity. In embodiments illustrated in FIG. 4A, a 1504 line/mm grating is followed by a fused silica prism in intimate contact (GRISM), such that the angular dependence of refraction at the output face provides the dispersion correction. The apex angle of the prism is 60 degrees, and the input beam intersects the grating face at an angle of 44.1 degrees. The spectral dispersion as a function of wavenumber varies now by 3.3% and still exhibits the characteristic quadratic distortion. Thus, as illustrated in FIG. 4B, using a GRISM dispersive assembly 430 as illustrated in FIG. 4A may lower the variation in dispersion to about 5.0%. Such a GRISM configuration may be useful for spectrometers with bandwidths ranging from about 1000 cm$^{-1}$ to about 3000 cm$^{-1}$.

As illustrated in FIG. 5A, the rays 550 image further from the optical axis than is desirable. The quadratic distortion is substantially equivalent in function to an extension in magnification along the dispersive plane, with pincushion-like distortion behavior. As illustrated in FIG. 5B, the addition of compensating barrel distortion in the spectrometer imaging lens can offset this pincushion distortion.

Referring now to FIG. 6A, a spectrometer including a dispersive assembly and a distortion element in accordance with some embodiments of the present inventive concept will be discussed. In particular, a distortion element, for example, wavefront modifier 640, is included to introduce barrel distortion, which compensates for the pincushion distortion discussed above with respect to FIGS. 5A and 5B, such that the variation in frequency spacing as imaged along the linear detection array will be no greater than about 1%. The dispersive assembly 630 illustrated in FIG. 6A is similar to the dispersive assembly discussed in the Hu patent discussed above. The addition of the distortion element in the system of FIG. 6A may reduce the resultant dispersion nonlinearity to about 0.4%, an order of magnitude improvement over the uncompensated result as illustrated in FIG. 6B. Thus, the high dispersion, 100 nm, 1295 cm$^{-1}$ system illustrated in FIG. 6A provides a variation in dispersion of substantially less than the 5.0% discussed above.

As illustrated in FIG. 6A, the distortion element (wavefront modifier 640) is positioned between the imaging lens 618 and the array detector 620. However, it will be understood that embodiments of the present inventive concept are not limited to this configuration. Embodiments will be discussed below including an asphere positioned after an uncompensated lens assembly and before the detector array. It will be understood that the distortion element can be accomplished using methods other than a wavefront modifier and can be designed into the optical train, or added to the optical train as an ancillary element without departing from the scope of the present inventive concept.

Referring now to FIG. 7A, a system with twice the total dispersion (half the total bandwidth): 53 nm, 648 cm$^{-1}$ than the system discussed above with respect to FIG. 6A will be discussed. In embodiments illustrated in FIG. 7A, the dispersive assembly 730' is provided by two strong dispersive stages. The first stage is a 1504 line/mm grating with a 43.4 degree angle of incidence, followed by a second stage GRISM including a 1504 line/mm grating at 46.8 degree angle of incidence on a 60 degree fused silica prism. The output from the first grating impinges upon the second stage grism, increasing the total dispersion to the target level. Exiting from the output face of the second prism, the dispersive function is linearized with respect to wavenumber to within 0.5% (FIG. 7B) using similar imaging optics 718, including pincushion distortion compensation 740, as discussed with respect to the 100 nm embodiments of FIG. 6A.

Referring now to FIG. 8A, a 22 nm bandwidth (259 cm$^{-1}$), where once again the dispersion variation is constrained to below 0.6% (FIG. 8B) will be discussed. As illustrated in FIG. 8A, the dispersive assembly 830" includes two strong dispersive stages. The first stage is a GRISM comprising a 2189 line/mm grating with a 67.2 degree angle of incidence on an 85.5 degree fused silica prism, followed by an equivalent second stage GRISM at 60 degree angle of incidence using similar imaging optics 818, including pincushion distortion compensation (840), as discussed above with respect to the 100 nm embodiments of FIG. 6A.

Referring now to FIG. 9A, a system with 270 nm bandwidth (5020 cm$^{-1}$) will be discussed. In embodiments illustrated in FIG. 7A, the dispersive assembly 930' is provided by two dispersive stages. The first stage is a 1504 line/mm grating with a 34.6 degree angle of incidence, followed by a second stage prism with apex angle equal to 31.5 degrees and angle of incidence of −21.4 degrees. The prism material of the current embodiment is optical glass with refractive index 1.717 and Abbe dispersion value 29.5. The prism is followed by a third stage incorporating a second grating. The second grating is a 956 line/mm grating at −19.0 degree angle of incidence.

The output from the first stage grating impinges upon the second stage prism which, in combination with the third stage second grating decreases the total dispersion to the target level and corrects the variation of dispersion with wavenumber. Exiting from the output face of the second grating, the dispersive function is linearized with respect to wavenumber to within 0.5% (FIG. 9B) using similar or equivalent imaging optics 918, including pincushion distortion compensation 940, as discussed with respect to the 100 nm embodiments of FIG. 6A.

Figure 12:
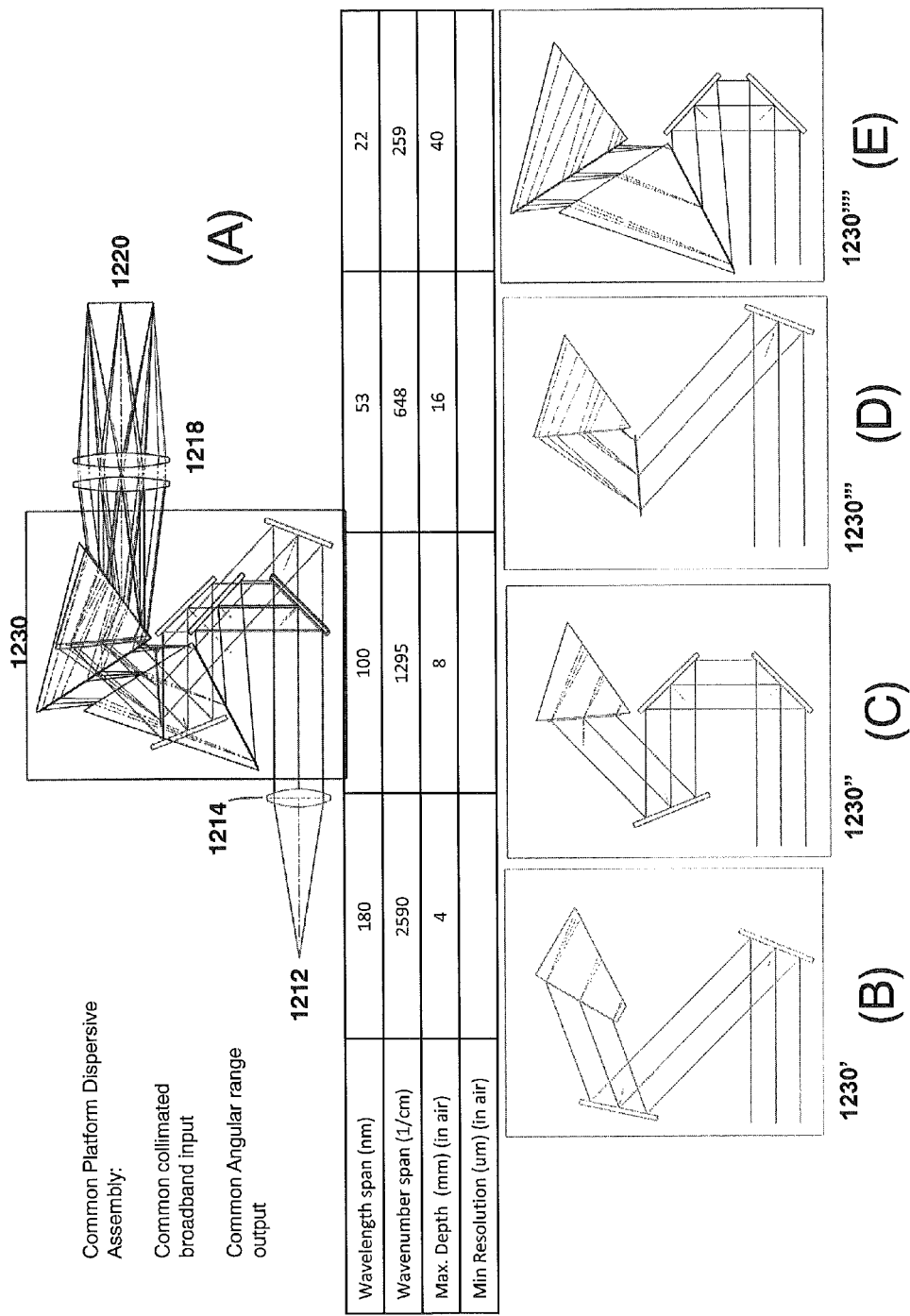
FIG. 12A is a block diagram of a spectrometer including a dispersive assembly in accordance with some embodiments of the present inventive concept.
FIGS. 12B-12E are block diagrams illustrating various dispersion assemblies in accordance with some embodiments of the present inventive concept.
Figure 14:
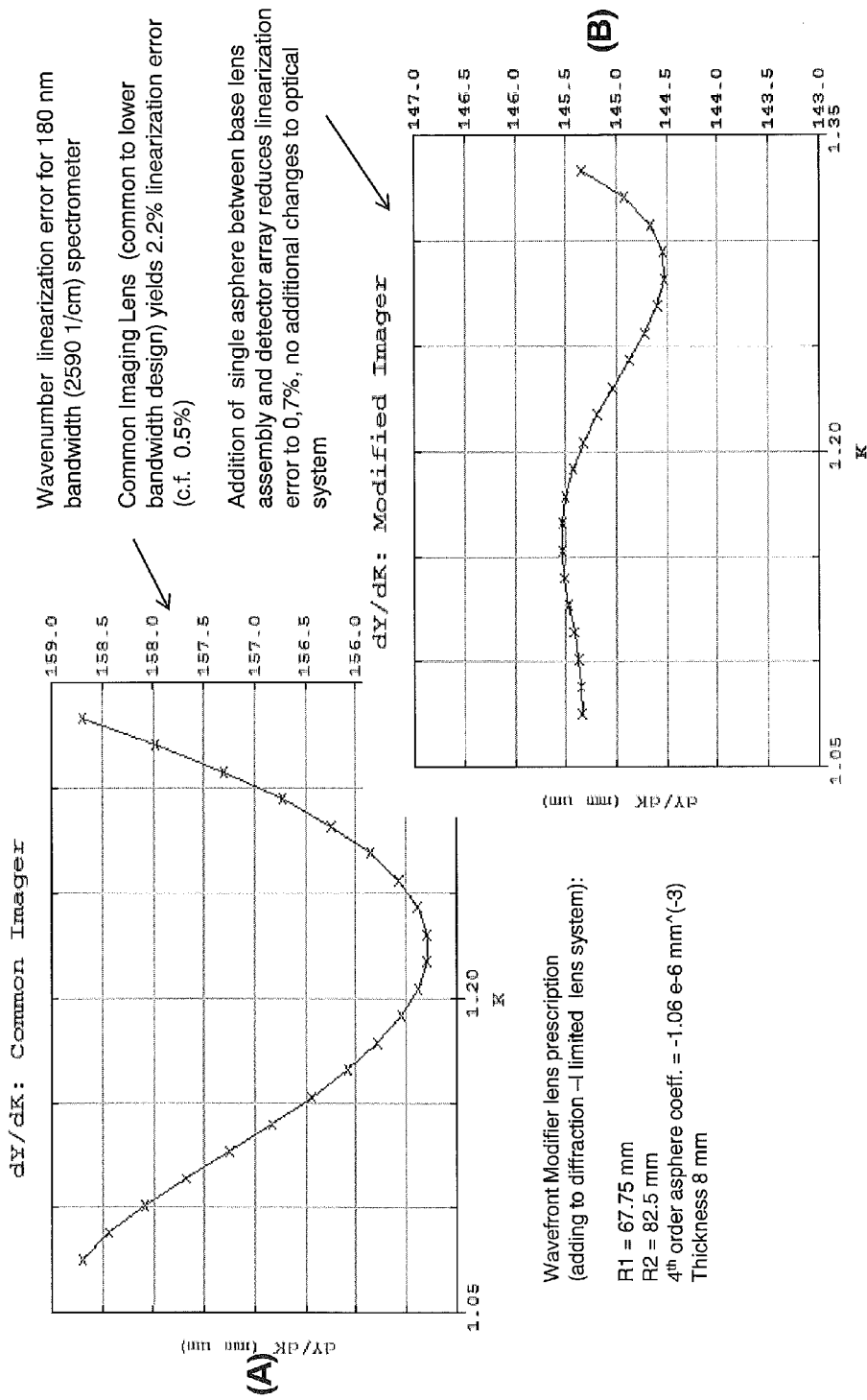
FIGS. 14A and 14B are graphs illustrating linearization error for both a common imager and a modified imager including an asphere in accordance with some embodiments of the present inventive concept.
Figure 15:
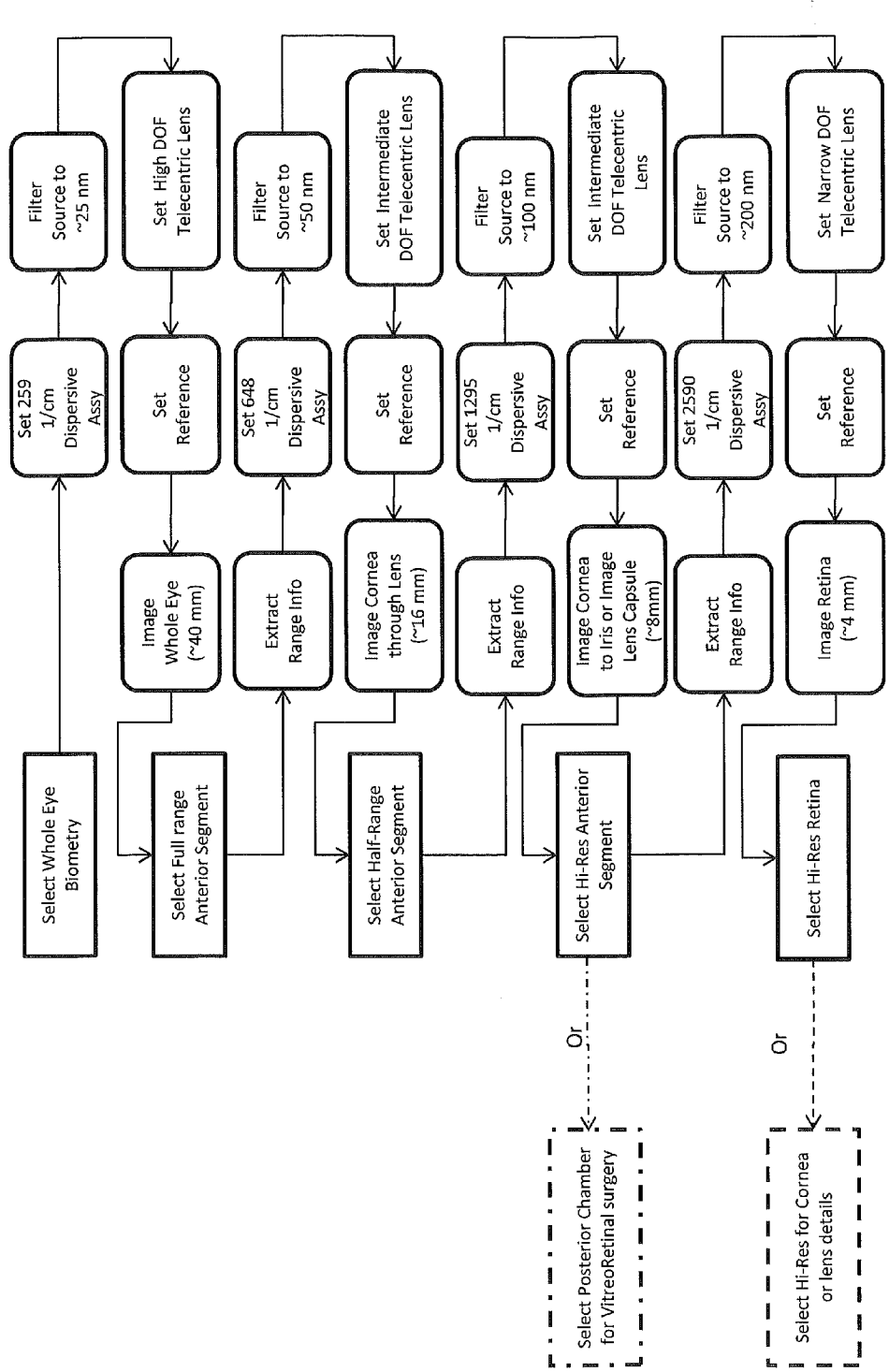
FIG. 15 is a detailed flow chart illustrating operations of spectrometers in accordance with some embodiments of the present inventive concept.

As illustrated in the table of FIG. 12, a system with 180 nm bandwidth (2590 cm$^{-1}$) can also be realized. In particular, a dispersive assembly including a GRISM including a 770 line/ mm grating with a 50.5 degree angle of incidence on a 32.6 degree fused silica prism may be used. This system may use similar imaging optics and pincushion distortion compensation as discussed above with respect to the 100 nm embodiments of FIG. 6A. With the broad bandwidth in these embodiments, the wavenumber linearization error may be about 2.0%.

Addition of an asphere lens as a wavefront modifier is demonstrated to improve wavenumber linearization error from about 2.2% to about 0.7 as illustrated in FIGS. 14A and 14B. In particular, linearization error for a common imaging lens (i.e. without a wavefront modifier) is about 2.2%, but with the addition of the asphere lens, the linearization error is reduced to about 0.7%. The asphere lens has a first surface radius of curvature R1=67.75 mm, a second surface radius of curvature R2=82.5 mm, a thickness of 8.0 mm, and a fourth order asphere coefficient of $-1.06\text{e-}6\ \text{mm}^{-3}$. The asphere lens is added to the system between the common lens assembly and the detector array, and in this embodiment is placed 22 mm in front of the detector array. Thus, the addition of the asphere lens may not require any modification of the lens assembly or spacing adjustments between the lens assembly and detector array. In other words, there are no additional changes to the optical system but for the addition of the asphere lens. Accordingly, in some embodiments the addition of the asphere lens is a drop-in improvement. One skilled in the art will recognize that while the use of a single asphere to compensation quadratic pincushion distortion offers certain design benefits, this distortion may be alternatively compensated in a multi-element lens set comprising spherical lens elements.

The versatility of embodiments of the present inventive concept may lead to a novel and flexible spectrometer design with a number of key attributes. For example, spectrometers in accordance with embodiments discussed herein may provide a) an ability to transform an input dispersive function to a target output function; b) a target output function that is linear in wavenumber to better than about 1.0%; c) an optical imaging system that operates independently of the dispersive range as long as certain input conditions are met; d) re-use of high cost dispersive components and e) accommodate bandwidth ranges from about 250 $\text{cm}^{-1}$ to about 5100 $\text{cm}^{-1}$.

Figure 10:
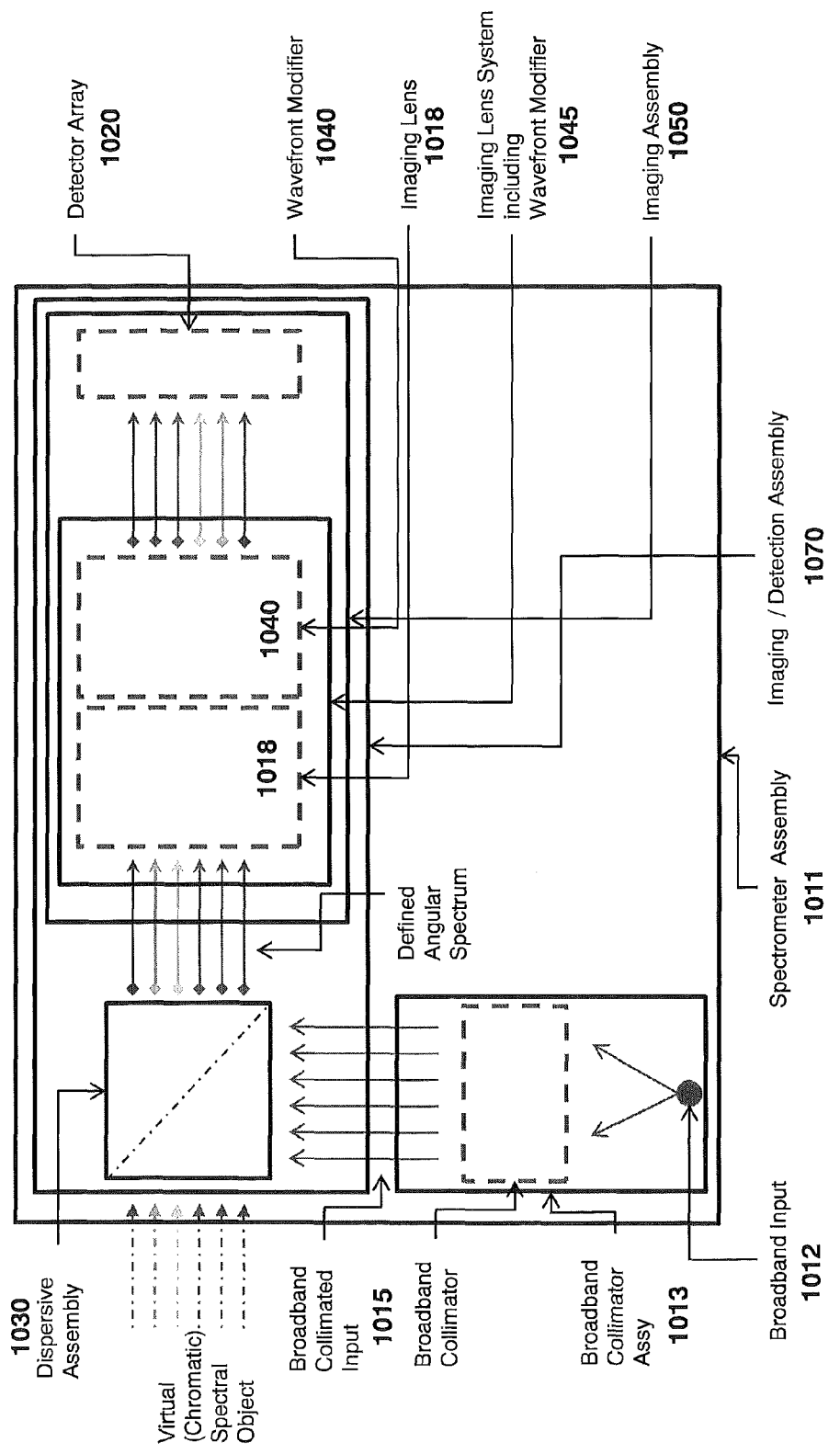
FIG. 10 is a block diagram illustrating a spectrometer including a dispersive assembly and a distortion element in accordance with some embodiments of the present inventive concept.

Referring now to FIG. 10, a block diagram of a spectrometer assembly 1011 in accordance with some embodiments of the present inventive concept will be discussed. As illustrated in FIG. 10, the spectrometer assembly 1011 includes a broadband collimator assay 1013, a dispersive assembly 1030, and an imaging/detection assembly 1070. The broadband input 1012 is provided to a broadband collimator 1014, part of the broadband collimator assay 1013. The broadband input 1012 from, for example, a single mode fiber, is collimated 1014 and the collimated input 1015 is provided to the dispersive assembly 1030. The dispersive assembly 1030 acts to create a virtual object at infinity with a given angular extent and an effective entrance pupil at a given distance from the spectrometer imaging lens 1018. The spectrometer imaging lens 1018, any wavefront modifier 1040 (distortion element) and the detector array 1020 are included in the image/detection assembly 1070. The imaging lens 1018 and wavefront modification 1040 make up the imaging lens system 1045. The dispersive assembly 1030 maps the input optical frequency spectrum to an angular spectrum as a function of wavenumber, and the imaging lens system 1045 further maps this angular spectrum to the detector array 1020.

The interface between the dispersive assembly 1030 and the spectrometer imaging assembly 1050 is defined by several constraints. The angular range of the dispersive assembly output is matched to the acceptance angle of the downstream imaging system. A second constraint is that output beams of the dispersive assembly pass through an effective exit pupil at a location that coincides with and is smaller than the entrance pupil of the subsequent imaging system. Additionally, to achieve a final detected spectrum that is linear in wavenumber, the angular rate of dispersion of the dispersive assembly must be symmetric about the central wavenumber of the source spectrum with a second-order variation that is matched to the compensating distortion in the imaging system. The latter criterion also includes embodiments for which the dispersive assembly 1030 has negligible second-order variation in the angular dispersion for which an imaging lens assembly without significant distortion may be employed.

When these conditions are met, the imaging system in accordance with various embodiments discussed herein may be paired and interfaced to a plurality of spectral sources and dispersive assemblies. This makes for a flexible spectrometer architecture, some of which are set out in the Table of FIG. 13, with maximum re-use of imaging elements across a broad range of dispersive power. This flexibility lends itself to a robust variable-dispersion spectrometer. In particular, in some embodiments, a series of discrete dispersive assemblies may be formulated such that they share a common angular range for different spectral ranges, and may be assembled on a movable stage. Each of these dispersive assemblies may be positioned in the spectrometer assembly before the common imaging optical assembly, such that the angular extent matches the entrance pupil location and field extent of the optical system. Since the input to the dispersive assembly is a single collimated beam, a sequence of fold mirrors may be deployed to align the input beam to the input orientation of any one of the various interchangeable dispersive assemblies, examples of which will be discussed below.

As each unique dispersive assembly is positioned within one common spectrometer assembly, a key attribute of the spectrometer is modified within one system architecture sharing other critical and costly components and, therefore, provides a series of discrete unique systems within one platform. Notable in Spectral Domain Optical Coherence Tomography (SDPCT), this structure enables dynamic switching among the attributes that define the trade-off between axial resolution and imaging depth: imaged bandwidth and frequency sampling interval.

Figure 11:
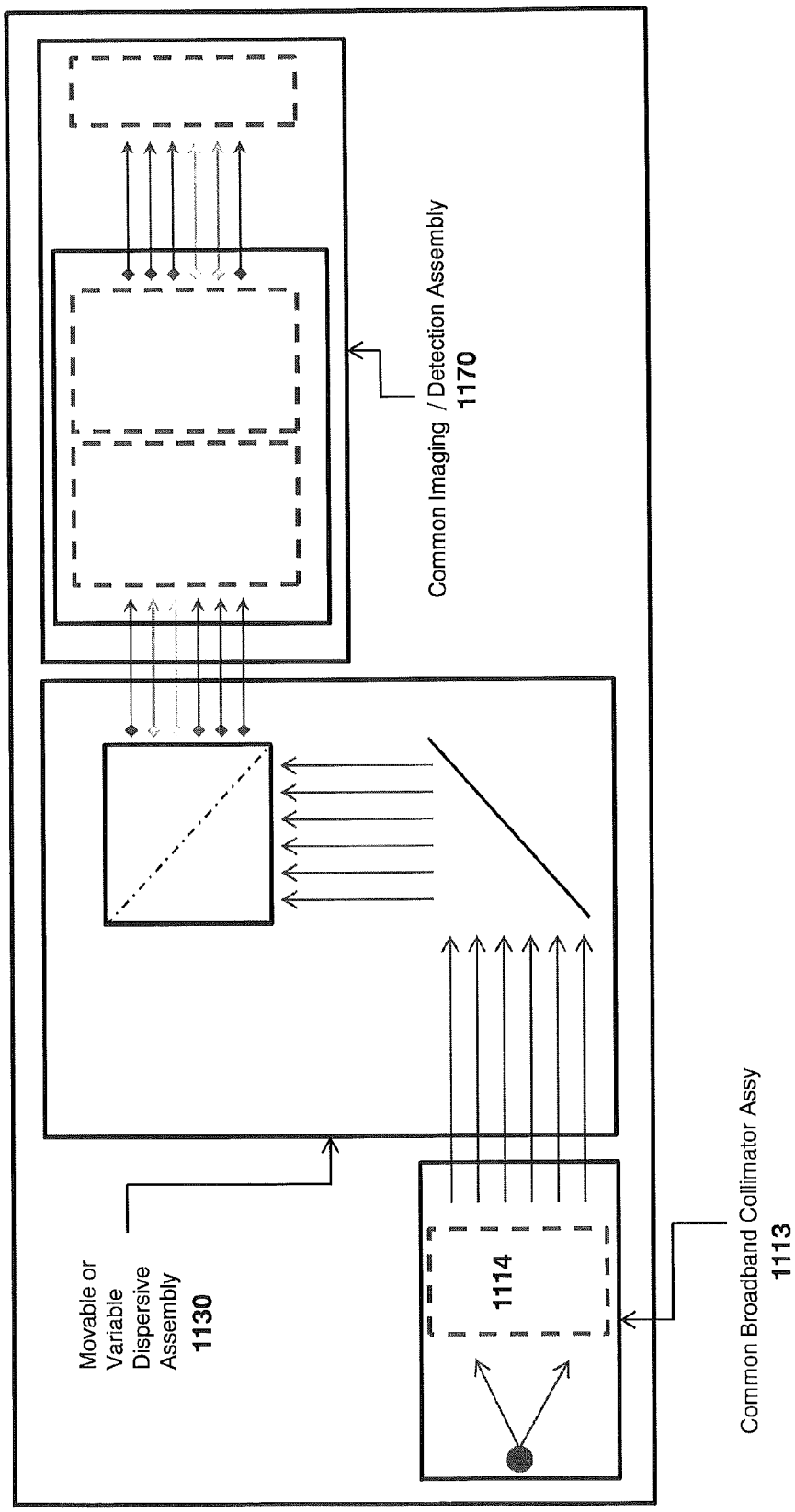
FIG. 11 is a block diagram illustrating a spectrometer including a dispersive assembly and a distortion element in accordance with some embodiments of the present inventive concept.

As illustrated in FIG. 11, the spectrometer architecture includes the various elements discussed with respect to FIG. 10, in particular, the common broadband assay 1112 including the broadband collimator 114; a moveable or variable dispersive assembly 1130; and a common imaging/detection assembly 1155 including the imaging lens 1118, wavefront modification 1140 (distortion correction) and the detector array 1120. As discussed above, the dispersive assembly 1130 may be configured to be interchangeable, i.e., the dispersive assembly and be taken out and replace with one of a number of other dispersive assemblies to create a new spectrometer architecture, thus providing the flexibility discussed above. The dispersive assemblies may include any of the dispersive assemblies discussed above or any similar assembly with unique attributes meeting the described constraints without departing from the scope of the present inventive concept.

It will be understood that although embodiments of the present inventive concept are discussed with respect to interchangeable dispersive assemblies, embodiments of the present inventive concept are not limited to this configuration. For example, any one or more of the spectrometer architectures discussed above may be manufactured as a standalone spectrometer without interchangeable parts without departing from the scope of the present inventive concept.

Referring now to FIGS. 12A-E, the dispersive assembly 1230 illustrated in FIG. 12A may be replaced by any of the dispersive assemblies 1230', 1230'', 1230''' and 1230'''' illustrated in FIGS. 12B-12E respectively. Thus any of the set of wavenumber-linearized dispersive assemblies (12B-12E) covering an order of magnitude in wavenumber range may be dropped into a common optical platform, i.e. the spectrometer illustrated in FIG. 12. Like reference numerals refer to like elements through and, thus, the details of the spectrometer will not be repeated herein. According to some embodiments of the inventive concept illustrated in FIGS. 12A-12E, a spectrometer system for four distinct dispersive assemblies covering from 2590 cm$^{-1}$ (inverse centimeters) to 259 cm$^{-1}$ may be provided. The details of each of these exemplary systems are detailed in the Table of FIG. 13.

For a spectrometer having a fixed detector array, i.e. defined by a number of detection elements and spacing therebetween, the finest axial resolution is limited by the total spectral bandwidth, and the maximum imaging depth is constrained by the finest frequency sampling interval; high resolution mandates wide bandwidth, with limited depth, and deep imaging requires fine sampling interval over a narrow bandwidth, and therefore poor axial resolution.

For Optical Coherence Tomography applications using a 4096 element detector array, such as a Basler Sprint CMOS array that is commercially available, embodiments discussed herein may provide one master system with variable depth ranging (as measured in air) from about 4.0 mm to about 40 mm, respectively, and with minimum axial resolutions from about 17 µm to about 1.7 µm, respectively. This may enable a single system for ocular applications ranging, for example, from ultra-high resolution of the retina to whole eye biometry (axial length measurements), providing exceptional economy of scale for ocular research, clinical examinations, and intrasurgical imaging. Such a system would allow very unique applications. For example, in ophthalmology, whole eye imaging with an order of magnitude dynamic range in depth and resolution attributes would allow single platform integration of high speed optical biometry (measurement of eye length and distances between all eye structures along the optical axis) using the 22 nm dispersive assembly, full 3D imaging of the entire anterior segment from cornea apex to posterior lens capsule in the setting with the 53 nm dispersive assembly, zooming in to the anterior chamber or lens capsule alone at the 100 nm setting, and observing tissue fine structure in the cornea or retina at the broadest bandwidth setting. In each case, optical resolution is optimized for the depth range of interest, and all measurements are accomplished with the same optical engine. This zoom function has never previously been demonstrated for spectral domain OCT.

In accordance with some embodiments, the zoom capability offers unique opportunity to perform whole eye analytics at multiple scales with a single console. One such work flow is outlined in the flowchart of FIG. 13. As illustrated therein, first, the axial properties of the whole eye are imaged using the narrowest bandwidth dispersive system, appropriately filtered source (to avoid excess radiation outside of the detected band), and a deep depth of field (DOF) telecentric optic. This first image set provides eye length as well as a signature that indicates distances to all key features in the eye, albeit with limited resolution of, for example, 20 µm. This distance map then provides distance values for feeding into the instrument settings to image specific regions of the eye as desired.

Stepping up in bandwidth, the next region might be to image the full anterior segment from cornea apex to behind the lens capsule, covering all of the refractive elements of the eye in one view, with a 16 mm range at better than 10 um resolution. Switching to retinal imaging optics, this 16 mm view would provide a broader range of the posterior chamber than has been heretofore possible, and may be vital to certain types of vitreoretinal surgery.

The next step in bandwidth enables an 8 mm view at better than 5 micron resolution for anterior chamber imaging from cornea to iris, or imaging of the entire lens capsule at high resolution. The 8 mm view may also be an appropriate window for vitreoretinal surgery.

And finally, ultrahigh resolution imaging of any specific targeted structures from retina to cornea, with bandwidths from 100 nm to 300 nm, and correspondingly restricted depths, is enabled.

It will be understood that the configurations discussed herein are not limited to the wavelength range or bandwidths, to wavenumber linearized systems, to application in OCT, or to applications in ophthalmology. For example, embodiments discussed herein may be used in Raman or near infrared (NIR) spectroscopy, for example, where a broadband bandwidth has utility in uncovering a broad fingerprint response, and a narrower bandwidth enables examination of spectroscopic fine structure. Others skilled in their respective art will find other applications and other detailed implementations that are served by the concepts of this inventive concept.

In the drawings and specification, there have been disclosed exemplary embodiments of the inventive concept. However, many variations and modifications can be made to these embodiments without substantially departing from the principles of the present inventive concept. Accordingly, although specific terms are used, they are used in a generic and descriptive sense only and not for purposes of limitation, the scope of the inventive concept being defined by the following claims.

That which is claimed is:

1. A wavenumber linearized spectrometer, the spectrometer comprising:

an input configured to receive broadband electromagnetic radiation from an external source;

collimating optics configured to collimate the received electromagnetic radiation;

a dispersive assembly comprising at least three elements, the at least three elements including:

a first diffractive element arranged to receive the collimated electromagnetic radiation wavefront and to disperse the collimated input radiation wavefront into a wavenumber-dependent angular spectrum;

a second diffractive element arranged to receive an electromagnetic radiation wavefront, said wavefront having been first dispersed into a wavenumber-dependent angular spectrum by the action of at least the first diffractive element, and arranged to disperse the input wavenumber-dependent angular spectrum into an output wavenumber-dependent angular spectrum different from the incident spectrum; and a refractive element configured to receive an electromagnetic radiation wavefront, said wavefront having been first dispersed into a wavenumber-dependent angular spectrum by the action of at least the first diffractive element, and configured to transform an input wavenumber-dependent angular spectrum into an output wavenumber-dependent angular spectrum different from the incident spectrum; and a detector array positioned to receive at least a portion of the dispersed spectrum of electromagnetic radiation after passing through an optical path that includes the set of collimating optics, a first diffractive element, a second diffractive element and a refractive element,
wherein the dispersive actions of at least the first diffractive element, the second diffractive element and the refractive element cooperate to disperse a substantially collimated source of broadband electromagnetic radiation such that the wavenumber increment is substantially constant with respect to spatial increment along the detector array.

2. The spectrometer of claim 1, wherein the refractive element further comprises a prism.

3. The spectrometer of claim 2, wherein a variation in frequency spacing along the detection array is no greater than 5.0%.

4. The spectrometer of claim 1, wherein the refractive element comprises an imaging lens assembly configured to image with pincushion distortion, the imaging lens assembly further comprising pincushion distortion correction, the presence of the pincushion distortion correction reducing a variation in frequency spacing along the detection array to no greater than about 1.0%.

5. The spectrometer of claim 4, wherein the pincushion distortion correction comprises a wavefront modifier element positioned after a lens set that images with pincushion distortion and before the detector array.

6. The spectrometer of claim 5, wherein the wavefront modifier element comprises an asphere.

7. The spectrometer of claim 1, wherein the dispersive assembly is configured to be interchangeable.

8. The spectrometer of claim 1, wherein a wavenumber span ranges from about 250 cm-1 to about 5100 cm-1.

9. A wavenumber linearized spectrometer, the spectrometer comprising:
an input configured to receive broadband electromagnetic radiation from an external source;
collimating optics configured to collimate the received electromagnetic radiation;
a dispersive assembly comprising at least three elements, the at least three elements including:
a first diffractive element arranged to receive the collimated electromagnetic radiation wavefront and to disperse the collimated input radiation wavefront into a wavenumber-dependent angular spectrum;
a second diffractive element arranged to receive an electromagnetic radiation wavefront, said wavefront having been first dispersed into a wavenumber-dependent angular spectrum by the action of at least the first diffractive element, and arranged to disperse the input wavenumber-dependent angular spectrum into an output wavenumber-dependent angular spectrum different from the incident spectrum; and
an imaging lens assembly configured to receive an electromagnetic radiation wavefront, said wavefront having been first dispersed into a wavenumber-dependent angular spectrum by the action of at least the first diffractive element, and configured to transform an input wavenumber-dependent angular spectrum into an output wavenumber-dependent angular spectrum different from the incident spectrum, the imaging lens assembly including a means for pincushion distortion correction; and
a detector array positioned to receive at least a portion of the dispersed spectrum of electromagnetic radiation after passing through an optical path that includes the set of collimating optics, a first diffractive element, a second diffractive element and an imaging lens assembly,
wherein the dispersive actions of at least the first diffractive element, the second diffractive element and the imaging lens assembly cooperate to disperse a substantially collimated source of broadband electromagnetic radiation such that the wavenumber increment is substantially constant with respect to spatial increment along the detector array.

10. The spectrometer of claim 9, wherein the distortion correction comprises an asphere positioned after a lens set in the imaging lens assembly, the presence of the distortion correction reducing variation in frequency spacing along the detection array to no greater than about 5.0%.

11. The spectrometer of claim 9, wherein the dispersive assembly is configured to be interchangeable.

12. The spectrometer of claim 9, wherein a wavenumber span ranges from about 1000 cm-1 to about 3000 cm-1.

13. A spectrometer, the spectrometer comprising:
an input configured to receive broadband electromagnetic radiation from an external source;
collimating optics configured to collimate the received electromagnetic radiation;
a dispersive assembly comprising at least three elements, the at least three elements including:
a first diffractive element arranged to receive the collimated electromagnetic radiation wavefront and to disperse the collimated input radiation wavefront into a wavenumber-dependent angular spectrum;
a second diffractive element arranged to receive an electromagnetic radiation wavefront, said wavefront having been first dispersed into a wavenumber-dependent angular spectrum by the action of at least the first diffractive element, and arranged to disperse the input wavenumber-dependent angular spectrum into an output wavenumber-dependent angular spectrum different from the incident spectrum; and
a refractive element configured to receive an electromagnetic radiation wavefront, said wavefront having been first dispersed into a wavenumber-dependent angular spectrum by the action of at least the first diffractive element, and configured to transform an input wavenumber-dependent angular spectrum into an output wavenumber-dependent angular spectrum different from the incident spectrum; and
a detector array positioned to receive at least a portion of the dispersed spectrum of electromagnetic radiation after passing through an optical path that includes the set of collimating optics, a first diffractive element, a second diffractive element and a refractive element,
wherein the dispersive actions of at least a first diffractive element, a second diffractive element and a refractive element cooperate to disperse a substantially collimated source of broadband electromagnetic radiation such that wavenumber increment is substantially constant with respect to spatial increment along the detector array.

14. The spectrometer of claim 13, wherein the dispersive assembly is configured to be interchangeable.

15. The spectrometer of claim 13, wherein a wavenumber span ranges from about 100 cm-1 to about 3000 cm-1.

16. The spectrometer of claim 13, wherein the refractive element comprises a prism.

17. The spectrometer of claim 13, wherein the refractive element comprises an imaging lens assembly.

18. The spectrometer of claim 17, wherein the imaging lens assembly comprises pincushion distortion correction.

* * * * *